Aug. 19, 1958 PAUL K. FUJIHARA Plant Pat. 1,743
PEACH TREE
Filed Dec. 13, 1957
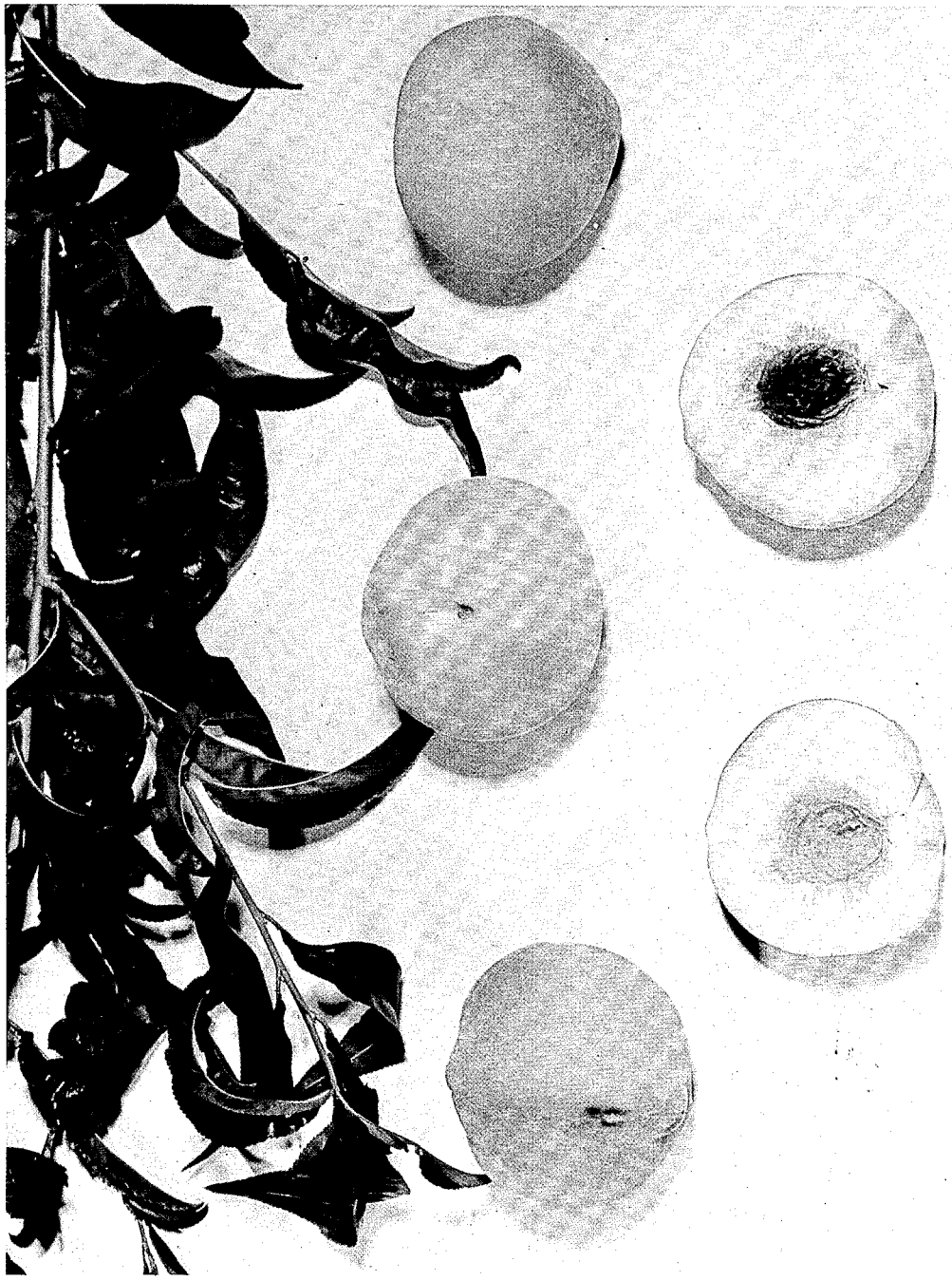
PAUL K. FUJIHARA
INVENTOR
HUEBNER & WORREL
ATTORNEYS
BY Richard M. Worrel United States Patent Office Plant Pat. 1,743
Patented Aug. 19, 1958

1,743

PEACH TREE

Paul K. Fujihara, Del Rey, Calif.

Application December 13, 1957, Serial No. 702,743

1 Claim. (Cl. 47—62)

The present invention relates to a new and distinct variety of peach tree.

The new variety of peach tree disclosed herein was developed by me on my ranch at 10251 East American Avenue, Del Rey, California. To achieve this development, the Giant Babcock of my Plant Patent No. 1,353 was cross-pollinated with a Red Haven (unpatented), the Giant Babcock serving as the female and the Red Haven as the male. Thereafter, pits from the resulting fruit were removed and planted and the characteristics of the resultant seedlings were observed. Scions from shoots growing from these seedlings were subsequently grafted onto suitable peach seedling rootstock on my above designated ranch. It was found that the hereinafter described characteristics of the subject peach were successfully and consistently reproduced by the described asexual reproduction.

Observation of the new variety of peach tree with which the present invention is concerned indicates that it has the following characteristics believed to be novel. As compared with its parents, the subject peach tree blossoms from about March 6 to March 16 which is substantially concurrent with the Red Haven but about a week later than the Giant Babcock. Although blossoming about the same time as the Red Haven, the instant variety matures from between about August 1 to August 8 which is slightly more than a month after the Red Haven and about two weeks after the Giant Babcock. In addition, the fruit is firm and has good shipping qualities; a relatively high sugar content and low acid content. It keeps for relatively long periods of time, and it has more red and yellow color than its maternal parent, the Giant Babcock. Further, it has been found that the fruit can remain on the tree for ten days to two weeks after ripening without becoming soft; this is in contrast to the Red Haven which gets soft in two or three days and the Giant Babcock which usually softens in about one week.

The accompanying drawing, which is a dye transfer print of a colored photograph, shows typical specimens of the fruit and foliage of the subject peach tree taken shortly after being picked early in August. The colors are as nearly true as is reasonably possible in a color representation of this type.

The following is a detailed description of the characteristics of the new fruit in accordance with the outline suggested by U. P. Hedrick in his book entitled "Systematic Pomology" published in 1925, and the color terminology employed as derived from the "Dictionary of Color" by Maerz and Paul, second edition.

Tree:

*Size, figure and shape.*—Approximates the Giant Babcock and Red Haven.

*Productivity.*—Somewhat less than the Giant Babcock.

Branches:

*Color.*—Van Dyke Brown, Plate 7–11–A.

*Lenticels.*—Apparently present but difficult to discern with the naked eye.

*Surface character.*—Usual.

*Size.*—*Usual.*

Leaves: (Generally very similar to both parents.)

*Size.*—Vary widely in size but majority large.

*Length.*—Approximately five and one-half inches.

*Width.*—One and one-fourth inch to one and five-eighths inch.

*Shape.*—Usual (lanceolate); tends to curl less than the Giant Babcock but to fold and wrinkle more than the Giant Babcock.

*Color.*—Upper surface—Plate 21–C-5; lower surface more yellow and lighter than upper surface, 21–L–6.

*Marginal form.*—Minutely serrated.

*Glandular characteristics.*—Net-veined, pinnate.

*Petiole.*—Length—three-eighths of an inch; thickness—one-sixteenth of an inch.

Stem glands:

*Number.*—Two singles, a few doubles.

*Arrangement.*—On the base of the leaf on each side of the petiole, or the central vein of the leaf.

*Size.*—Minute.

*Type.*—Globose.

*Color.*—Same as the stem.

*Stipules.*—A pair present on each side of the base of the leaves.

Flower buds: Size, shape, surface, and other characteristics substantially the same as the Burbank July Elberta and the Giant Babcock.

Flowers: Substantially the same as the Giant Babcock and the Burbank July Elberta but blooms approximately ten days after the Giant Babcock in March.

Fruit:

*Maturity.*—About August 5.

*Size.*—Uniformity—large and uniform; axial diameter—three and one-half inches; transverse diameters in the suture plane—three and three-eighths inches; transverse diameters at right angles to the suture plane—three and five-eighths inches.

*Form.*—Uniformity—only slightly variable; nearly symmetrical; suture length—shallow on the dorsal side but distinct and extending from the base to the apex and becoming deeper at the base, generally indistinct on the ventral side except close to the base and apex although on one of the more ripe fruit, the suture was visible substantially the entire distance from the apex to the base on the ventral side; suture position—in the plane of symmetry.

*Ventral surface.*—Somewhat flat.

*Stem cavity.*—Pronounced and ovate; spanning dimensions—one-half inch minimum to seven-eighths inch maximum.

*Base.*—Flat but torus-like.

*Apex.*—Rounded and coming to a sharp point precisely at the apex.

*Stem.*—Caliper—five-sixteenths of an inch.

Skin:

*Thickness.*—Thin.

*Texture.*—Smooth.

*Tendency to crack.*—None.

*Color.*—Plate 47–J–1 and shading to Plate 2–C–11.

*Pubescence.*—Very slight satiny down.

Flesh:

*Color.*—Plate 10–J–5 with blotches of Plate 5–L–2.

*Color of pit well.*—Plate 2–L–6.

*Juice.*—Not too juicy.

*Flavor.*—Sweet, low acid content.

*Aroma.*—Ususal.

*Texture.*—Very crisp when observed a few days prior to full ripening but softening toward maturity.

*Fibers.*—Medium in size and texture.

*Eating quality.*—Excellent.

Stone:

*Type.*—Free stone—adheres to one pit cavity more than the other.

*Fibers.*—Adheres to stone on side which is more difficult to detach.

*Size.*—Medium and smaller than Red Haven or Giant Babcock; one and one-half inches long by one and one-sixteenth inches wide by three-fourths of an inch thick.

*Form.*—Oval, pointed apex and flattened toward base.

*Base.*—Squared.

*Sides.*—Symmetrical.

*Ridges.*—Lie along approximately concentric arcs. more pronounced near apex where deep furrows are apparent.

*Size of grooves.*—Approximately one-eighth inch deep.

*Color.*—Cattail Cafe'Noir, Plate 8–H–12.

*Splitting tendency.*—None noticed.

Use: Canning, freezing, drying and fresh for local and long distance shipping.

Keeping quality: Excellent.

Shipping quality: Excellent.

Having thus described my new peach tree, I claim:

A new and distinct variety of peach tree substantially as shown and described herein and especially characterized by: high sugar and low acid content having an excellent flavor for eating purposes; an early blooming habit, later than the Giant Babcock and approximately concurrently with the Red Haven; ripening approximately two weeks later than the Giant Babcock and a month later than the Red Haven; more prominent red and yellow coloring of the fruit than the Giant Babcock; and a marked ability to hold on the tree in prime condition for longer periods of time after ripening than the Red Haven or the Giant Babcock.

No references cited.